United States Patent
Hayes et al.

(10) Patent No.: US 6,811,311 B2
(45) Date of Patent: Nov. 2, 2004

(54) PATIENT SUPPORT INCLUDING X-RAY CASSETTE SUPPORT WITH POSITION INDICATOR

(75) Inventors: Stephen Hayes, Dudley (GB); Stephen Hollyoak, Kingswinford (GB)

(73) Assignee: Huntleigh Technology PLC (GB)

( * ) Notice: Subject to any disclaimer, the term of this patent is extended or adjusted under 35 U.S.C. 154(b) by 0 days.

(21) Appl. No.: 10/221,230

(22) PCT Filed: Oct. 11, 2001

(86) PCT No.: PCT/GB01/04563

§ 371 (c)(1),
(2), (4) Date: Nov. 18, 2002

(87) PCT Pub. No.: WO02/30284

PCT Pub. Date: Apr. 18, 2002

(65) Prior Publication Data

US 2003/0179855 A1 Sep. 25, 2003

(30) Foreign Application Priority Data

Oct. 12, 2000 (GB) .............................................. 0025015

(51) Int. Cl.⁷ .............................................. G03B 42/04

(52) U.S. Cl. ........................ 378/181; 378/167; 378/177; 378/209; 5/601

(58) Field of Search ................................ 378/167, 177, 378/178, 179, 180, 181, 208, 209; 5/601

(56) References Cited

U.S. PATENT DOCUMENTS

| | | | |
|---|---|---|---|
| 2,989,634 A | 6/1961 | Ouid et al. | |
| 3,826,922 A | 7/1974 | Ingles | |
| 4,193,148 A | 3/1980 | Rush | |
| 4,651,364 A | 3/1987 | Hayton et al. | |
| 4,893,323 A | 1/1990 | Cook, III | 378/208 |
| 4,916,725 A | 4/1990 | Quinter et al. | |
| 5,155,758 A | 10/1992 | Vogl | |
| 5,222,115 A | 6/1993 | Highgenboten | |
| 5,422,928 A | 6/1995 | Payne | |
| 5,475,884 A | 12/1995 | Kirmse et al. | |
| 5,703,925 A | 12/1997 | Wright | |
| 5,996,149 A | 12/1999 | Heimbrock et al. | |

*Primary Examiner*—David V. Bruce
*Assistant Examiner*—Allen C. Ho
(74) *Attorney, Agent, or Firm*—Brown Raysman Millstein Felder & Steiner

(57) ABSTRACT

A patient support comprising a frame 22 supporting a translucent support surface 24 elevated above the frame 22 by frame members 23. The members 26 support an x-ray cassette tray 36 for sliding movement along the length of the frame 22. The x-ray cassette trays 36 can be loaded onto the members 26 from either or both the head 30 and foot 32 ends of the frame 22. All of the patient support surface can be covered by the x-ray cassettes. In use, the x-ray cassette tray 36 is pulled out from the members 26 and loaded with an x-ray cassette 53. The handle 39 is pulled out from within the tray 36 and locked into position against latch 38. The tray 36 is then slid back onto the members 26 and the position of the cassette 53 within the tray 36 is indicated by the position of the indicator 65 visible along the side of the frame 22.

7 Claims, 3 Drawing Sheets

// PATENT SPECIFICATION

PATIENT SUPPORT INCLUDING X-RAY CASSETTE SUPPORT WITH POSITION INDICATOR

This application is a National Phase entry of PCT International Application, Serial No. PCT/GB01/04563, filed 11 Oct. 2001, and claims priority from Great Britain Application No. 0025015.9, filed 12 Oct. 2000.

BACKGROUND OF THE INVENTION

The present invention relates to a patient support apparatus, and more particularly, to a patient support apparatus having an x-ray cassette support.

It is known to have stretchers or beds in hospitals used in emergency room settings where they are used to serve a variety of functions. For example, the stretcher or bed may serve as a bed whilst a patient is awaiting treatment, and may also be used to transport the patient. Frequently, the stretcher or bed also serves as an examination table, surgery table and an x-ray table for taking x-rays of patients before, during, or after surgical operations.

Typical stretchers or beds that also serve as x-ray tables have an x-ray cassette support which is located beneath an x-ray transparent horizontal bed surface.

It is known that such beds or stretchers need accessories to position the x-ray cassette under the bed surface. In order to take the x-rays, a positioning rod with a hook at its end, is used to engage a handle of the x-ray cassette tray to position the tray under the bed surface. Graduations are provided on the rod so that the x-ray cassette tray can be located in the same position for a succession of photographs.

The frame supporting the stretcher or bed surface has a graduated scale along the length of at least one side. The units of the graduated scale of the rod correspond to the units of the graduated scale of the frame. The rod graduated scale can increase numerically from the handle end to the engaging means end or from the engaging means end to the handle end.

In use, the technician looks at the frame scale from the side of the apparatus, and determines the frame scale number that is adjacent the body section to be x-rayed. The technician then walks to the foot end of the frame, engages the rod with the x-ray cassette tray and pushes the rod until the rod scale number corresponding with the desired frame scale number appears in line with the end of the frame. In this way, the apparatus provides for accurate positioning of the x-ray cassette tray.

However, the process of determining the frame scale and each corresponding rod graduation for a particular position of x-ray is time consuming and tedious.

SUMMARY OF THE INVENTION

The present invention seeks to provide a patient support apparatus with an improved x-ray tray positioning means, overcoming the disadvantages of the prior art.

Accordingly, the present invention provides a patient support apparatus having a frame supporting a surface for a patient to lie on, the frame comprising means to support at least one x-ray cassette tray along its length under the patient surface, the x-ray cassette tray housing an x-ray cassette, the x-ray cassette tray provided with means for movement thereof, such that in use, the moving means provides a direct reference to the position of the x-ray cassette within the tray under the patient surface.

Preferably, the moving means is a handle with an indicator corresponding to the top edge of the x-ray cassette and more preferably, the indicator is visible along the side of the frame under the patient support surface. In this way the handle is pushed to position the x-tray cassette to the required position, the position of the indicator along the side of the frame showing exactly where the x-ray cassette is under the patient support surface. There is no requirement to match numbers along the frame and the means for pushing the x-ray tray as with the prior art.

Preferably, the handle is stored within the tray when not in use. The handle may also be telescoping or rotatably mounted to allow for storage within the tray when not in use.

The invention will now be described by example and with reference to the following drawings in which:

DETAILED DESCRIPTION OF THE PREFERRED EMBODIMENTS

Figure 1:
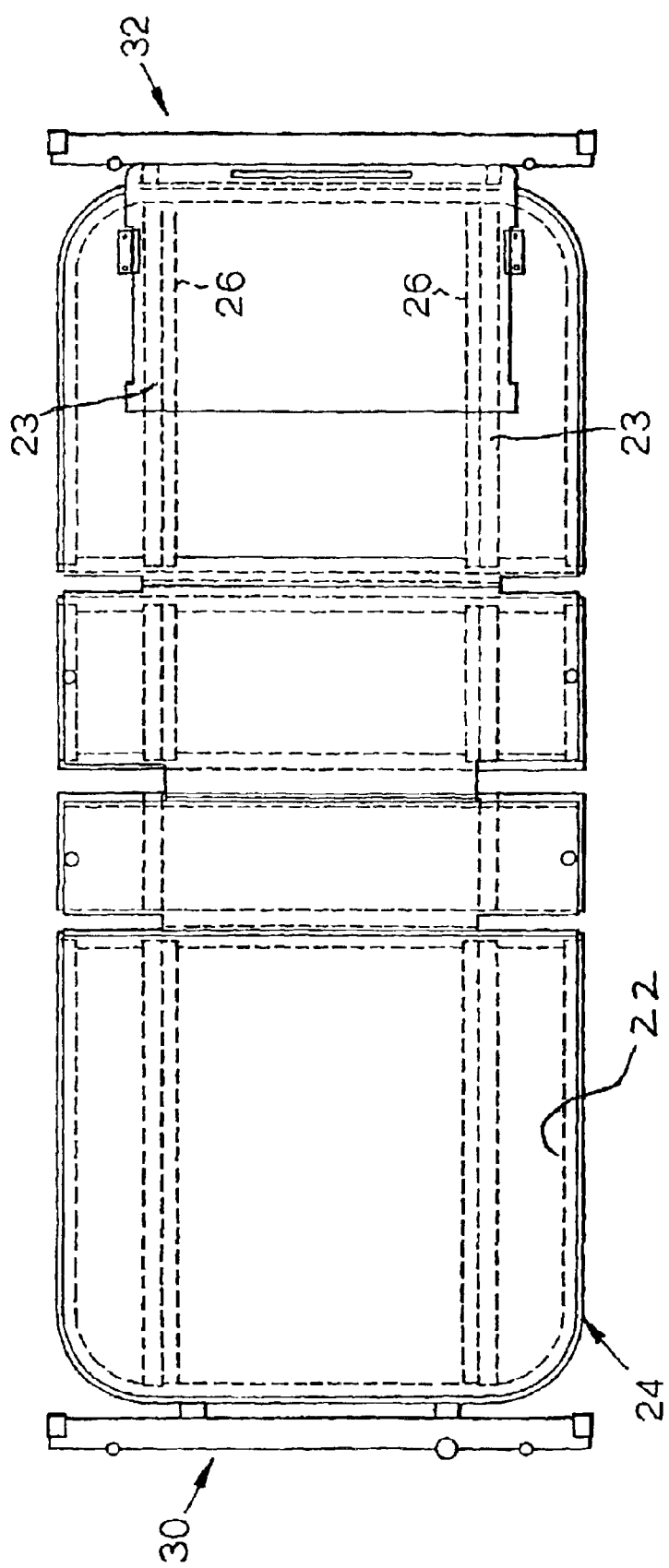
FIG. 1 is a schematic plan view of a patient support surface according to the invention.

Referring generally to FIG. 1, a patient support is shown as having a translucent patient support surface 24 supported by a frame 22.

Figure 2:
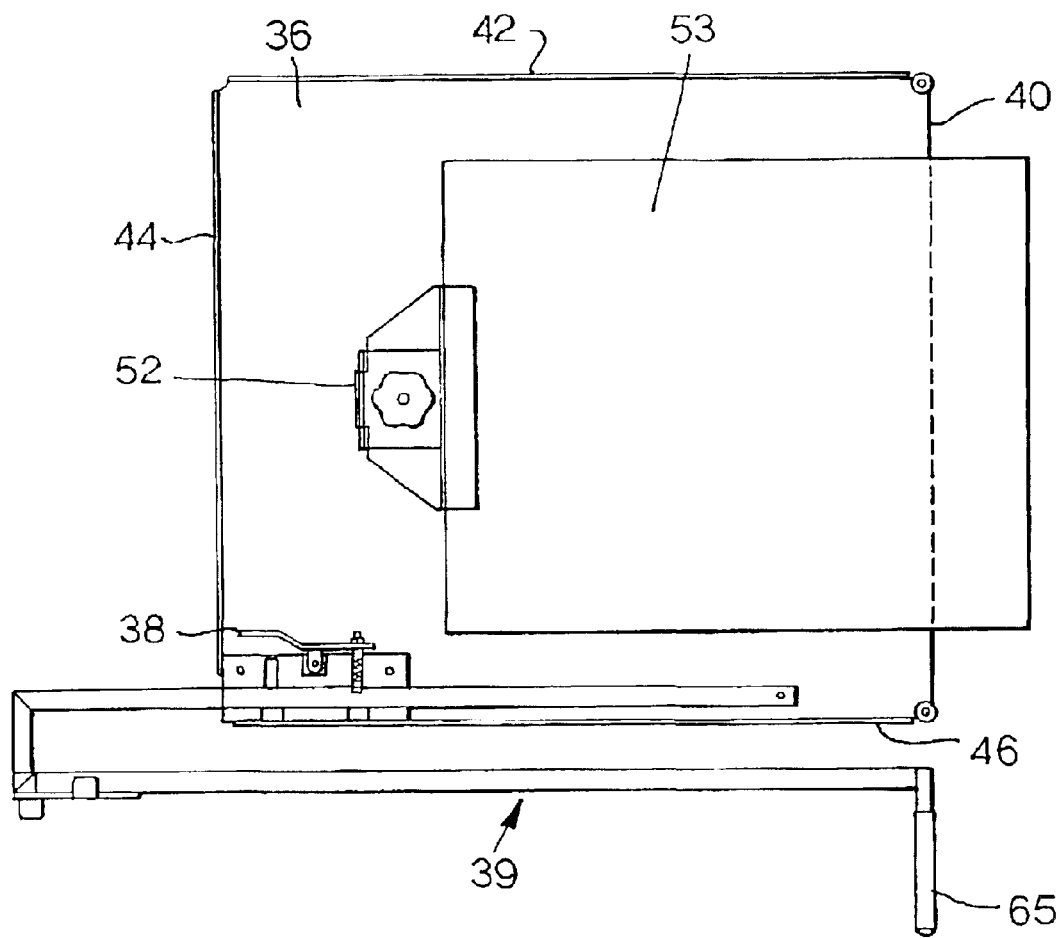
FIG. 2 shows an x-ray cassette tray in the stored position.
Figure 3:
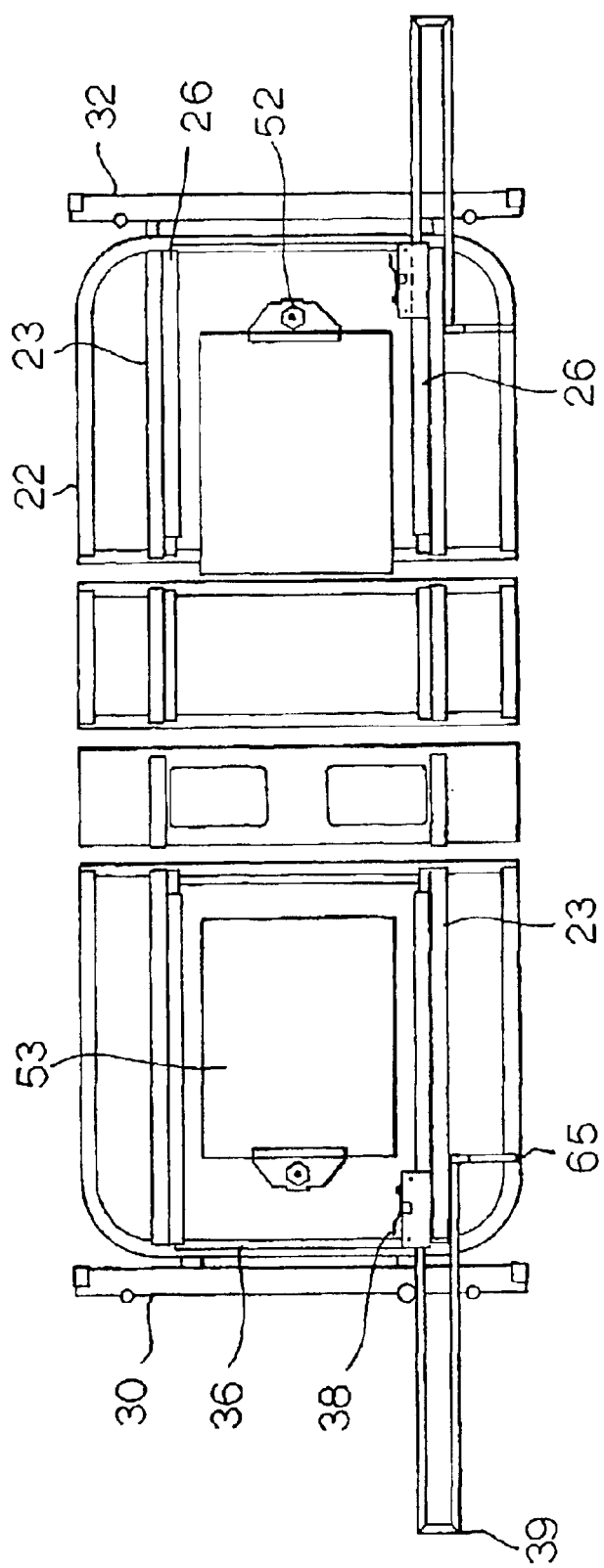
FIG. 3 is a schematic plan view of the patient support frame showing the cassette trays in the in-use positions at the head and foot ends of the support.

The frame 22 supports a support surface 24 which is elevated above the frame 22 by frame members 23. The support surface 24 and any mattress (not shown) are selected to be x-ray transparent. An x-ray cassette tray 36 as shown in FIG. 2, is located at the head 30 and/or the foot 32 ends of the frame 22 between the frame 22 and the support surface 24.

The x-ray cassette tray 36 has sides 40, 42, 44 and 46. The side 46 has a latch 38 co-operating with a handle 39 for easily transporting and positioning the tray 36. A clamp 52 on the x-ray tray 36 is used for securing the x-ray cassette 53 onto the tray 36.

The frame 22 includes longitudinal support members, optionally channels, 26 to support the x-ray cassette tray 36 for sliding movement along the length of the frame 22. The x-ray cassette trays 36 can be loaded onto the members/channels 26 beneath the support surface 24 from either or both the head 30 or foot 32 ends of the frame 22. The x-ray cassette trays 36 can then each be moved along the members/channels 26 towards the middle of the patient support surface. Therefore, all or almost all of the patient support surface can be covered by the x-ray cassettes.

A handle 39 for accurately positioning the x-ray cassette tray 36 beneath the patient support surface 24 is normally stored within the tray. During use the handle 39 is pulled out to extend beyond the cassette tray 36 and secured in position against a latch 38. In the extended, in use, position an indicator 65 on the handle 39 corresponds directly with the top edge of the x-ray cassette within the tray. The handle 39 is slidable within the x-ray cassette tray 36, but can also be telescoping or rotatably mounted (not shown).

In use, the x-ray cassette tray 36 is pulled out from the members/channels 26 and loaded with an x-ray cassette 53 which is secured by clamp 52. The handle 39 is pulled out from within the tray 36 and locked into position against latch 38. The loaded x-ray cassette tray 36 is then slid back onto the members/channels 26 from the head end 30 or foot end 32 as desired, and the position of the cassette 53 within the tray 36 is indicated by the position of the indicator 65 visible along the side of the frame 22.

Therefore, all the physician or technician has to do is to push the handle 39 until the indicator 65 corresponds to the patient area to be x-rayed. The indicator 65 is easily visible on the side of the frame 22 and provides a direct reference point to the position of the x-ray cassette under the patient support surface 24. The physician and/or technician do not have to measure the rod or scale or estimate where the x-ray cassette is. The indicator 65 provides a direct reference to the position of the x-ray cassette under the patient support surface 24.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A patient support apparatus comprising a frame supporting a surface for a patient to lie on, the frame including means to support at least one X-ray cassette tray along its length under the patient surface, the X-ray cassette tray adapted for housing an X-ray cassette, the X-ray cassette tray provided with a handle for movement of the tray, the handle comprising an indicator corresponding to an edge of the x-ray cassette, such that in use the handle provides a direct reference to the position of the X-ray cassette under the patient surface.

2. The patient support apparatus of claim 1, wherein the indicator is visible along the side of the frame.

3. The patient support apparatus of claim 1, wherein the handle is storable within the tray.

4. The patient support apparatus of claim 3, wherein the handle is telescoping or rotatably mounted to allow for storage within the tray when not in use.

5. A patient support apparatus comprising a frame supporting a patient surface for a patient to lie on, the frame adapted for supporting along its length an X-ray cassette tray beneath the patient surface, the X-ray cassette tray adapted for housing an X-ray cassette, the X-ray cassette tray selectably positionable along the length of the frame and comprising a handle adapted for positioning the tray along the length of the frame and for providing a direct indication of the position of the X-ray cassette under the patient surface, the handle storable within the X-ray cassette tray when not in use.

6. The patient support apparatus of claim 5, wherein the handle is telescoping or rotatably mounted to allow storage within the X-ray cassette tray.

7. A patient support apparatus comprising a frame supporting a patient surface for a patient to lie on, the frame supporting along its length at least one X-ray cassette tray beneath the patient surface, the X-ray cassette tray adapted for housing an X-ray cassette, the X-ray cassette tray selectably positionable along the length of the frame and comprising a position indicator providing a direct indication of the position of the x-ray cassette under the patent surface, wherein the position indicator is configured for alignment with an edge of a housed X-ray cassette.

* * * * *